United States Patent [19]

Esders et al.

[11] 4,275,152
[45] Jun. 23, 1981

[54] HYDROLYSIS OF PROTEIN-BOUND CHOLESTEROL ESTERS

[75] Inventors: Theodore W. Esders, Webster; Charles T. Goodhue, Rochester; Christine A. Michrina, Webster, all of N.Y.

[73] Assignee: Eastman Kodak Company, Rochester, N.Y.

[21] Appl. No.: 62,433

[22] Filed: Jul. 30, 1979

Related U.S. Application Data

[63] Continuation of Ser. No. 765,168, Feb. 3, 1977, abandoned.

[51] Int. Cl.³ .............................................. C12Q 1/60
[52] U.S. Cl. ........................................ 435/11; 435/19; 435/198; 435/52; 435/822; 435/921; 435/939
[58] Field of Search ..................................... 435/11, 19

[56] References Cited

U.S. PATENT DOCUMENTS

| | | |
|---|---|---|
| 3,689,364 | 9/1972 | Hartel ..................................... 435/19 |
| 3,703,591 | 11/1972 | Bucolo et al. ........................... 435/19 |
| 3,759,793 | 9/1973 | Stork ..................................... 435/198 |
| 3,869,349 | 3/1975 | Goodhue et al. ....................... 435/11 |
| 3,898,130 | 8/1975 | Komatsu ................................ 435/198 |
| 3,925,164 | 12/1975 | Beaucamp et al. ..................... 435/11 |
| 4,042,461 | 8/1977 | Esders et al. .......................... 435/11 |
| 4,052,263 | 10/1977 | Masurekov et al. ................... 435/11 |
| 4,161,425 | 7/1979 | Perry ..................................... 435/11 |
| 4,164,448 | 8/1979 | Röeschlau et al. ..................... 435/11 |

FOREIGN PATENT DOCUMENTS

| | | | |
|---|---|---|---|
| 811728 | 6/1974 | Belgium .................................... | 435/11 |
| 2509156 | 9/1975 | Fed. Rep. of Germany . | |
| 2522432 | 12/1975 | Fed. Rep. of Germany . | |
| 1395126 | 4/1975 | United Kingdom . | |
| 1435400 | 5/1976 | United Kingdom ..................... | 435/11 |

OTHER PUBLICATIONS

Helenius et al., Biochemistry, vol. 10, No. 13, p. 3 (1971).

*Primary Examiner*—Alvin E. Tanenholtz
*Attorney, Agent, or Firm*—J. Jeffrey Hawley

[57] ABSTRACT

A novel process is described for hydrolyzing protein-bound cholesterol esters such as are found in blood serum. The method comprises contacting sample containing protein-bound cholesterol esters with a compatible mixture of an enzyme preparation which demonstrates cholesterol ester hydrolase activity and, as an effector, a surfactant which is an alkyl phenoxy polyethoxy ethanol comprising a polyoxyethylene chain of less than about 20 oxyethylene units.

Hydrolysis compositions comprising compatible mixtures of an enzyme preparation which demonstrates cholesterol ester hydrolase activity and an effector which is a surfactant as described are also disclosed, as are analytical elements comprising at least one layer which includes such a hydrolysis composition.

17 Claims, No Drawings

HYDROLYSIS OF PROTEIN-BOUND CHOLESTEROL ESTERS

This is a continuation of application Ser. No. 765,168, filed Feb. 3, 1977 and now abandoned.

FIELD OF THE INVENTION

The present invention relates to methods for the hydrolysis of cholesterol esters and more particularly to methods and compositions for the hydrolysis of protein-bound cholesterol esters such as serum cholesterol esters.

BACKGROUND OF THE INVENTION

In the assay of body fluids, especially blood serum, for cholesterol concentration, the initial step requires hydrolysis of cholesterol esters to free cholesterol.

Conventional procedures for cholesterol ester hydrolysis use a strong base (KOH, NaOH, etc.), or for reasons of simplicity and selectivity, a hydrolase enzyme (i.e., a cholesterol esterase). Handling of caustic materials may be inconvenient or undesirable and, as discussed in relation to prior publications below, while enzymatic techniques can be useful for the hydrolysis of "free" cholesterol esters, i.e., those not bound to protein, they are either ineffective or very slow when used to treat protein-bound cholesterol esters. The binding of the ester to protein apparently inhibits the action of the esterase and thus requires some means for breaking the protein-ester complex before the enzyme can act on the ester.

U.S. Pat. No. 3,869,349 issued Mar. 4, 1975 to Goodhue et al describes an improved technique for hydrolyzing serum cholesterol esters which involves the use of compositions comprising a lipase preparation which demonstrates cholesterol esterase activity and a protease. This patent contains no suggestion that a surfactant can replace the protease.

U.S. Pat. No. 3,703,591 to Bucolo et al describes the use of a combination of a lipase and a protease to achieve serum (i.e., protein-bound) triglyceride hydrolysis. No suggestion is made to use a surfactant either in combination with or as a substitute for the protease in the hydrolysis of cholesterol esters.

U.S. Pat. No. 3,759,793 to Stork et al describes the hydrolysis of serum triglycerides using a lipase from *Rhizopus arrhizus* which is apparently identical to that suggested by Bucolo et al, however, with no requirement for a protease. The reasons for this apparent anomaly are not clear; however, it is noted in British Pat. No. 1,395,126 of the same assignee that the Stork et al hydrolysis technique is very slow. This British Patent describes an improved method for hydrolyzing triglycerides with the aforementioned *Rhizopus arrhizus* lipase comprising contacting the triglyceride with the lipase in a buffer and in the presence of carboxylesterase and an alkali metal or alkaline earth metal alkyl sulfate, the alkyl radical of which contains 10 to 15 carbon atoms. The preferred alkyl sulfate is sodium dodecyl sulfate. There is no suggestion that the use of surfactant alone in the absence of carboxylesterase stimulates hydrolase activity of triglycerides.

Helenius, Ari and Simons, Kai, *Biochemistry*, Vol. 10, No. 13 (1971) describe a method for removing all major lipids from human plasma low-density lipoprotein comprising treatment of the human plasma with high concentrations of natural and synthetic surfactants. Lipid removal is applied for purposes of characterizing the lipid free protein moiety of human plasma low-density lipoprotein. There is no suggestion in this publication that the combination of a surfactant and a lipase would yield a useful analytical tool which would simplify the assay of serum for cholesterol content by providing a fast and accurate hydrolysis method and a stable assay composition.

U.S. Pat. No. 3,689,364 issued Sept. 5, 1972 describes an assay for lipase contained in body fluids such as blood serum using a "free" triglyceride emulsion as substrate for the lipase. It is suggested that the bile salts which stabilize the substrate emulsion of "free" triglyceride (i.e., triglycerides not bound to protein) also concurrently exert an "activating effect" on the lipase under assay when it is a pancreatic lipase. The activating effect apparently results in an increase in the hydrolytic activity of the lipase on the free triglycerides of the substrate emulsion. There is no teaching or suggestion in this patent that such bile salts exert any effect on lipase preparations when contacted with lipids bound to proteins as are found in blood serum. In particular there is no suggestion that such lipase can hydrolyze protein-bound cholesterol esters.

U.S. Pat. No. 3,898,130 to Komatsu issued Aug. 5, 1975 describes a method for hydrolyzing triglycerides comprising contacting triglyceride with a composition comprising a mixture of a microbial lipase, particularly Candida lipase (sic), a pancreatic lipase and a bile salt selected from sodium taurodeoxycholate, taurocholate, taurochenodeoxycholate and taurodehydrocholate. Both the microbial and the pancreatic lipase enzymes are critical components of the hydrolysis composition.

German Offenlegungsschrift No. 2,522,432 published Dec. 4, 1975 describes an enzymatic method for hydrolyzing cholesterol esters using a cholesterol esterase from *Pseudomonas fluorescens*. There is no suggestion of the use of or a need for a surfactant to achieve protein-bound cholesterol ester hydrolysis.

French Pat. No. 2,223,696 and U.S. Pat. No. 3,925,164 issued Dec. 9, 1975 describe an assay for total cholesterol in blood serum wherein cholesterol esters are hydrolyzed with an enzyme preparation from *Candida rugosa*, Rhizopus or Aspergillus in the presence of a surfactant. The only suggested surfactant is hydroxypolyethoxy dodecane. As will be shown in the examples below, such surfactants are not as effective as the materials described herein, possibly because of incompatibility with the cholesterol ester hydrolase.

German Offenlegungsschrift No. 2,509,156 published Sept. 23, 1975 describes an enzymatic method for the assay of total cholesterol using as the cholesterol ester hydrolyzing medium cholesterol esterase and a gallic acid or a salt of a gallic acid. The cholesterol esterase is identified as EC 3.1.1.13 which is derived from *Nocardia restrictus*. There is no suggestion in the foregoing publication that the synthetic surfactants described herein are useful effectors for cholesterol esterase.

RELATED APPLICATIONS

Commonly-owned U.S. Application Ser. No. 715,798 filed on Aug. 19, 1976, entitled "Hydrolysis of Protein-Bound Triglycerides" discloses a process and a composition for hydrolyzing protein-bound triglycerides, featuring a compatible mixture of an enzyme preparation and a surfactant.

SUMMARY OF THE INVENTION

It has now been discovered that protein-bound cholesterol esters can be hydrolyzed in relatively short periods of time on the order of less than about 10 minutes (preferably in about 5 minutes) by contacting the protein-bound cholesterol esters with a compatible mixture of a lipase preparation which demonstrates cholesterol ester hydrolase activity and an alkyl phenoxy polyethoxy ethanol comprising a polyoxyethylene chain of less than about 20 oxyethylene units.

The techniques and compositions described herein permit the use of a much broader range of enzyme preparations as cholesterol ester hydrolyzing agents than has been possible with prior art methods. Thus, lower cost materials can be used to attain reaction times and states of reaction completeness at least equal to and often superior to those attainable with the prior art methods and materials.

DESCRIPTION OF THE PREFERRED EMBODIMENTS

As discussed hereinabove, there are enzyme preparations which catalyze the hydrolysis of free cholesterol esters. Such materials, however, catalyze the hydrolysis of cholesterol esters bound to protein, as found in blood serum, only at very slow rates or in an incomplete fashion. This result is apparently due to some effect of the protein-lipid complex which prevents the enzyme from catalyzing the hydrolysis in the usual fashion. The prior art has suggested the use of what might be termed effectors, namely, agents which increase the rate at which lipase materials can hydrolyze protein-bound cholesterol esters. Although the mechanism by which such agents act is not known, it is theorized that they disrupt the ester-protein complex in some way to "free" the ester for hydrolysis in a conventional mode. Protease enzymes, for example, have been suggested for this purpose.

We have found that certain surfactants are effectors and may be used as substitutes for protease to render useful, as hydrolyzers of protein-bound cholesterol esters, enzyme preparations which are normally incapable of catalyzing the hydrolysis of protein-bound cholesterol esters or which catalyze such hydrolysis only at undesirably slow rates. Furthermore, since protease tends to degrade proteinaceous binders, such as gelatin, used in multilayer elements for the detection of analyte as described in Belgian Pat. No. 801,742, the compositions described herein are particularly useful in such elements.

The novel hydrolysis compositions of the present invention thus comprise a compatible mixture of an enzyme preparation which demonstrates cholesterol esterase activity and as an effector a surfactant which is an alkyl phenoxy polyethoxy ethanol comprising a polyoxyethylene chain of less than about 20 carbon atoms.

Enzyme preparations potentially useful in the methods and compositions described herein are those demonstrating free (i.e., not protein-bound) cholesterol ester hydrolase activity. Lipase preparations which demonstrate such activity are specifically preferred.

A useful screening technique for determining the cholesterol ester hydrolase (esterase) activity of enzyme, and particularly lipase, preparations comprises adding a fixed amount of the enzyme preparation to a standard cholesteryl linoleate solution at pH 7.0, incubating at 37° C. under $N_2$ for 2 hours and determining the amount of ester left in the solution by the hydroxylamine method of J. Vonhoeffmyr and R. Fried, Z. Klin. Chem. U. Klin. Biochem., 8, 134 (1970). By means of this technique, any preparation which demonstrates a cholesterol esterase activity which releases above about 25 mg/dl cholesterol in the screening procedure should be considered a useful candidate in the practice of the present invention.

Useful enzyme preparations for cholesterol ester hydrolysis may be derived from plant or animal sources but we prefer preparations from microbial sources such as from *Candida rugosa, Chromobacterium viscosum,* variant *paralipolyticum,* crude or purified. Other useful enzyme preparations and methods for their preparation are described in the following U.S. Pat. Nos.: 2,888,385 to Grandel issued May 26, 1959; 3,168,448 to Melcer et al issued Feb. 2, 1965; 3,189,529 to Yamada et al issued June 15, 1965; 3,262,863 to Fukumoto et al issued July 26, 1966; and 3,513,073 to Mauvernay et al issued May 19, 1970.

Preferred commercial enzyme preparations include wheat germ lipase from Miles Laboratories of Elkhart, Indiana, Lipase 3000 from Wilson Laboratories, Steapsin from Sigma Chemical Company (both of the latter are pancreatic enzymes), and Lipase M (from *Candida rugosa*) from Enzyme Development Company.

Certain surfactants inhibit the cholesterol esterase activity of certain enzyme preparations. Consequently, it is important that before any attempt is made to combine an enzyme preparation and a surfactant for use as described herein some determination of the compatibility of the two members of the composition be made. Such a determination is preferably made by using the test described below. An enzyme preparation and surfactant mixture which successfully meets this test is referred to herein as a compatible mixture and each member thereof is said to be compatible with the other.

Hydrolysis compositions of the present invention are characterized by the test used in comparative Example II below. The proposed surfactant under evaluation is added to normal human serum. A sample of a proposed enzyme preparation is added and the mixture incubates at 37° C. for a period of about 10 minutes. Aliquots (0.1 ml) of this solution are then diluted to 1.9 ml with water and placed in a boiling water bath for 10 minutes. Cholesterol is quantified in a total volume of 1.2 ml by the well known cholesterol oxidase system described below. A similar "control" test is performed concurrently using only the enzyme preparation without the surfactant. When performing the foregoing test it is most desirable to run a blank which contains all of the components of the mixture but the enzyme preparation so that any reaction which may be due to free cholesterol or other components of the serum can be subtracted. The preferred compositions accomplish hydrolysis of at least 70% of the available cholesterol esters in less than 10 minutes and most preferred are those which achieve substantially complete hydrolysis, i.e., hydrolysis of at least about 90% of the available cholesterol esters in less than about 10 minutes.

From testing of this type, it has been discovered that phenoxy polyethoxy ethanols are highly superior effectors. Specifically preferred are materials available commercially from Rohm and Haas Company under the tradenames Triton X-114, 100, 102 and Triton n-101. Preferred alkyl phenoxy polyethoxy ethanols comprise a polyoxyethylene chain of less than about 20 oxyethylene units. As will be shown in the following examples, similar materials outside of these broad limits do not provide the improved hydrolysis described herein. Most preferred are those materials wherein the alkyl is either 8 or 9 carbon atoms.

As will be demonstrated in the examples below, certain prior art surfactants discussed above do not produce acceptably high dissociation when combined with the enzyme preparations evaluated. This includes the hydroxypolyethoxy dodecanes of French Pat. No. 2,223,696 and U.S. Pat. No. 3,925,164. (Exemplary useful hydrolysis compositions are shown in Table I.)

The concentration of enzyme preparation and surfactant in the compatible mixtures useful for hydrolysis according to the methods described herein can vary greatly depending, for example, on such factors as the purity of the enzyme preparation, the activity of the enzyme preparation, the nature of the bound cholesterol ester, the particular surfactant used, etc. Generally, however, surfactant concentrations of from about 0.25 to about 10% by weight of the analytical solution have been found useful with concentrations of between about 0.5 and 5% by weight of surfactant providing optimum results. The useful range of concentrations of enzyme preparation will vary similarly, but concentrations of between about 10 and 80 mg/ml of the total analytical solution have been found quite useful when commercial preparations are used. Optimization of any such composition is, of course, within the skill of the art.

It should be apparent that hydrolysis compositions of the type described herein can be incorporated into any of the single or multiple layer absorbent or other analytical elements (for example, test papers) described in the prior art and that the use of the compositions and methods described herein in such elements for the detection or determination of protein-bound cholesterol esters is within the scope of the invention.

In accordance with one preferred embodiment, the hydrolysis compositions described herein are incorporated into one or more layers of multilayer analytical elements of the type described, for example, in Belgian Pat. No. 801,742 and copending U.S. patent application Ser. No. 538,072 of Przybylowicz and Millikan entitled "Integral Analytical Element" which was filed Jan. 2, 1975. Such elements are intended to analyze liquids for the presence of a predetermined analyte and they include a preferably non-fibrous spreading layer, which delivers a uniform apparent concentration of analysis-active components in an applied sample to a reagent layer which contains at least some of the materials interactive in the presence of analyte to produce a detectable product or detectable change. Such layers are in fluid contact under conditions of use.

Reference herein to fluid contact between layers in an analytical element identifies the ability of a fluid, whether liquid or gaseous, to pass in such element between superposed regions of the spreading layer and the reagent layer. Stated in another manner, fluid contact refers to the ability of components of a fluid to pass between the layers in fluid contact. Although such layers in fluid contact can be contiguous, they may also be separated by intervening layers as described in detail hereinafter. However, layers in the element that physically intervene a spreading layer and reagent layer in mutual fluid contact will not prevent the passage of fluid between the fluid contacting spreading and reagent layers.

Fluid contact between layers can be achieved by preparing elements having layers that are initially contiguous or effectively so for purposes of fluid passage. Alternatively, it may be appropriate to prepare elements that have layers initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and U.S. Pat. No. 3,933,594. As will be appreciated, if the element has initially non-contiguous layers, it may be necessary to apply compressive force or otherwise provide means to bring layers of the element into fluid contact at the time of its use to provide an analytical result.

According to a highly preferred embodiment of such an element, the hydrolysis composition described herein is incorporated into the spreading layer and a detection system, for example, a cholesterol oxidase and an indicator composition sensitive to hydrogen peroxide for cholesterol detection, is included in the reagent layer.

The following description of standardized procedures and examples are presented to further illustrate the useful scope of the present invention.

STANDARD PROCEDURES

Quantification of Total Serum Cholesterol—Cholesterol esters must first be hydrolyzed to free cholesterol. Incubation mixtures contained in a total volume of 8 ml:2.4 units cholesterol oxidase (*N. cholesterolicum*), 0.768 mg 4-aminoantipyrene.HCl, 0.256 mg 1,7-dihydroxynaphthalene, 0.22 mg peroxidase (125 purpurogallin units/mg), 6.4 mg crude lipase preparation, and either 0.48 mg protease (*B. subtilis* (Sigma Corporation Type VII)) or 160 mg octyl phenoxy polyethoxy ethanol (Triton X-100). Incubation mixtures were equilibrated at 37° C. for five minutes and the reaction was initiated by addition of 20 μl of human serum. After 10 minutes, the absorbance at 490 nm was measured. Blank tubes contained all components except serum. Total cholesterol concentrations were obtained from a standard curve which was constructed by substituting aliquots of Fermco Test Aqueous Cholesterol Standard (available from Fermco Laboratories, Chicago, Illinois) for the serum substrate.

The reference method was the Liebermann-Burchard method as described in "Hawk's Physiological Chemistry", B. L. Oser (ed.), Ed. 14, McGraw-Hill Book Company, New York, 1964 (1965). This method involves extraction of the cholesterol and cholesterol esters from serum prior to quantitation.

EXAMPLE 1—ENZYME CATALYZED HYDROLYSIS OF SERUM CHOLESTEROL ESTERS IN THE PRESENCE OF ALKYL PHENOXY POLYETHOXY ETHANOL SURFACTANT

Human serum (20 μl) was added to 8 ml of buffer reagent (equilibrated at 37°) which contained either enzyme preparation and a protease or the enzyme preparation and surfactant to effect hydrolysis of the cholesterol esters. After 10 minutes, the absorbance at 490 nm was measured, and total serum cholesterol calculated as described above.

Serum cholesterol was quantified using the cholesterol oxidase, peroxidase system. In this system cholesterol esters are first hydrolyzed to free cholesterol which is subsequently oxidized to cholestenone with concomitant production of $H_2O_2$. The $H_2O_2$ is then coupled to dye formation via a peroxidase reaction. It has been reported that a crude lipase preparation catalyzes hydrolysis of serum cholesterol esters if a protease is added to the incubation mixture. The data in Table I show that in the presence of S-1 (an octylphenoxy polyethoxy ethanol having about 10 ethoxy units and an HLB number of 13.5) complete hydrolysis of cholesterol esters was observed. The surfactant efficiently replaced the protease and thus eliminated the need for this extraneous protein which may undesirably (1) hydrolyze protein components of the cholesterol detection system or (2) alter the pH of the system. Quantitation of serum cholesterol with a lipase preparation and S-1 as the hydrolytic system gave results (see Table I) which compared very favorably with the reference method.

TABLE I

| | Total Serum Cholesterol Concentration (mg/dl) | | |
|---|---|---|---|
| Sample | Lipase Protease (Control) | Lipase 2% S-1 | Reference Method[a] |
| 1 | 225 | 225 | 232 |
| 2 | 150 | 185 | 190 |
| 3 | 150 | 180 | 176 |
| 4 | 240 | 230 | 220 |

[a]The reference method was a semi-automated Liebermann-Burchard method

An S-1 concentration of 2% gave complete hydrolysis and the surfactant produced no harmful effects at concentrations as high as 4%. Although final color densities were measured after 10 minutes, reactions were essentially complete in as little as five minutes at 37° C.

COMPARATIVE EXAMPLE I

Repetition of the test described in Example I above using alkylphenoxy polyethoxy ethanols having polyoxyethylene chains above about 20 yields results which indicate that such surfactants somehow inhibit the cholesterol esterase activity of the enzyme.

COMPARATIVE EXAMPLE II

Direct comparative tests were conducted with a cholesterol esterase from *Candida rugosa* and (a) surfactant as described in French Pat. No. 2,223,696 and (b) representative of the surfactants described herein.

Incubation mixtures were prepared containing in a total volume of 0.6 ml:
  0.5 ml normal human serum
  20 mg cholesterol esterase (Lipase M commercial preparation from *Candida rugosa*)
  5 μmoles potassium phosphate buffer (pH 7.0)
  10 mg effector Reactions were allowed to proceed for 10 minutes at 37° C. and then 0.1 ml aliquots were added to 1.9 ml of water and placed in a boiling water bath for 10 minutes. Cholesterol was then quantitated via the cholesterol oxidaseperoxidase system using aqueous cholesterol standards to prepare a standard curve. The results of these tests are shown in Table II below.

TABLE II

| | mg/dl | | |
|---|---|---|---|
| Effector | Cholesterol Actual | Ester Recovered | % Recovery |
| None | 157 | 2.4 | 1.5 |
| Octylphenoxy polyethoxy ethanol | 157 | 157 | 100 |
| Polyoxyethylene (4) lauryl ether | 157 | 3.4 | 2.2 |
| Polyoxyethylene (23) lauryl ether | 157 | 103 | 65.7 |
| Polyoxyethylene (12) lauryl ether | 157 | 0 | 0 |

(The numbers in parentheses indicate the number of oxyethylene units.)

From the foregoing, it is apparent that the polyoxyethylene lauryl ethers (i.e., the dodecane materials of French Pat. No. 2,223,696) are not useful as effectors in accordance with the invention described herein.

The invention has been described in detail with particular reference to certain preferred embodiments thereof, but it will be understood that variations and modifications can be effected within the spirit and scope of the invention.

What is claimed is:

1. A process for hydrolyzing protein-bound cholesterol esters comprising contacting protein-bound cholesterol esters in an aqueous medium in the absence of protease with a compatible mixture of an enzyme preparation having cholesterol ester hydrolase activity and an alkyl phenoxy polyethoxy ethanol comprising a polyoxyethylene chain of less than about 20 oxyethylene units, said mixture containing an amount of said ethanol whereby said compatible mixture is effective to hydrolyze at least 70% of the cholesterol esters available in said aqueous medium.

2. A process for hydrolyzing blood serum cholesterol esters comprising contacting serum containing cholesterol esters in the absence of protease with a compatible mixture of an enzyme preparation having cholesterol ester hydrolase activity and as a surfactant an alkyl phenoxy polyethoxy ethanol comprising a polyoxyethylene chain of less than about 20 oxyethylene units, said mixture containing an amount of said ethanol whereby said compatible mixture is effective to hydrolyze at least 70% of the cholesterol esters available in said aqueous medium.

3. The process of claim 2 wherein the enzyme preparation is an esterase preparation derived from a microbial or an animal source.

4. The process of claim 3 wherein the esterase preparation is derived from a microbial source selected from the group consisting of *Candida rugosa*, *Chromobacterium viscosum*, variant *paralipolyticum*, and *Rhizopus arrhizus*.

5. The process of claim 4 wherein the esterase preparation is derived from *Candida rugosa*.

6. The process of claim 3 wherein the esterase preparation comprises a pancreatic esterase.

7. The process of claim 2 wherein the surfactant is an alkyl phenoxy polyethoxy ethanol of from about 7 to about 13 ethoxy units.

8. The process of claim 7 wherein the surfactant is an octyl phenoxy polyethoxy ethanol.

9. A process for hydrolyzing protein-bound cholesterol esters comprising contacting protein-bound cholesterol esters in an aqueous medium in the absence of protease with a compatible mixture of microbially derived enzyme preparation having cholesterol ester hydrolase activity and an effector which is an alkyl phenoxy polyethoxy ethanol comprising a polyoxyethylene chain of less than about 20 oxyethylene units, said mixture containing an amount of said ethanol whereby said compatible mixture is effective to hydrolyze at least 70% of the cholesterol esters available in said aqueous medium.

10. A composition for hydrolyzing protein-bound cholesterol esters in an aqueous medium comprising a compatible mixture free from protease and containing an enzyme preparation having cholesterol ester hydrolase activity and as a surfactant an alkyl phenoxy polyethoxy ethanol comprising a polyoxyethylene chain of less than about 20 oxyethylene units, said mixture containing an amount of said ethanol whereby said mixture is effective to hydrolyze at least 70% of the cholesterol esters available in said aqueous medium.

11. The composition of claim 10 wherein the enzyme preparation is an esterase preparation derived from a microbial or an animal source.

12. The composition of claim 11 wherein the esterase preparation is derived from a microbial source selected from the group consisting of *Candida rugosa, Chromobacterium viscosum,* variant *paralipolyticum,* and *Rhizopus arrhizus.*

13. The composition of claim 12 wherein the esterase preparation is derived from *Candida rugosa.*

14. The composition of claim 11 wherein the esterase preparation comprises a pancreatic esterase.

15. The composition of claim 11 wherein the surfactant is an alkyl phenoxy polyethoxy ethanol of from about 7 to about 13 ethoxy units.

16. A process for hydrolyzing cholesterol esters in a sample of blood serum comprising contacting said sample in a buffered aqueous medium in the absence of protease with a compatible mixture of an enzyme preparation having cholesterol ester hydrolase activity and an alkyl phenoxy polyethoxyethy ethanol comprising a polyoxyethylene chain of less than about 20 oxyethylene units, said mixture containing an amount of said ethanol whereby said mixture is effective to hydrolyze at least 70% of the cholesterol esters available in said aqueous medium.

17. A composition for hydrolyzing protein-bound cholesterol esters in a sample of an aqueous medium, said composition free from protease and comprising a buffer and a compatible mixture of an enzyme preparation having cholesterol ester hydrolase activity and an alkyl phenoxy polyethoxy ethanol comprising a polyoxyethylene chain of less than about 20 oxyethylene units, said composition containing an amount of said ethanol whereby said composition is effective to hydrolyze at least 70% of the cholesterol esters available in said sample.

* * * * *